United States Patent [19]

Totten et al.

[11] Patent Number: 4,868,192

[45] Date of Patent: Sep. 19, 1989

[54] PHARMACEUTICAL COMPOSITIONS AND METHODS USING CERTAIN 4H-PYRANO (3,2-G) QUINOLINE COMPOUNDS

[75] Inventors: Joseph W. Totten, Old Woodhouse; Kenneth A. Walters, Loughborough, both of England

[73] Assignee: Fisons plc, Ipswich, England

[21] Appl. No.: 167,343

[22] Filed: Mar. 14, 1988

[30] Foreign Application Priority Data

Mar. 17, 1987 [GB] United Kingdom ............... 8706242
Jan. 14, 1988 [GB] United Kingdom ............... 8800833

[51] Int. Cl.$^4$ ............................................. A61K 31/44
[52] U.S. Cl. ........................... 514/291; 514/861; 514/863; 514/830; 514/928
[58] Field of Search ......................................... 514/291

[56] References Cited

U.S. PATENT DOCUMENTS 4,419,352 12/1983 Cox et al. .......................... 514/291
4,474,787 10/1984 Cairns et al. ...................... 514/291
4,760,072  7/1988 Brown et al. ...................... 514/291

OTHER PUBLICATIONS

Chemical Abstracts, 103:196023 x, (1985).

*Primary Examiner*—Leonard Schenkman
*Attorney, Agent, or Firm*—Marshall, O'Toole, Gerstein, Murray & Bicknell

[57] ABSTRACT

A pharmaceutical composition comprising, as active ingredient, 9-ethyl-6,9-dihydro-4,6-dioxo-10-propyl-4H-pyrano(3,2-g)quinoline-2,8-dicarbo xylic acid or a pharmaceutically acceptable derivative thereof in admixture with a pharmaceutical acceptable adjuvant or excipient, the composition being suitable for topical administration to a patient's skin but not suitable for administration orally or to the patient's eye.

Also described are methods of treatment of various dermatological disorders comprising topical administration to the skin of a patient suffering from such a disorder of a therapeutically effective quantity of 9-ethyl-6,9-dihydro-4,6-dioxo-10-propyl-4H-pyrano(3,2-g)quinoline-2,8-dicarbo xylic acid or a pharmaceutically acceptable derivative thereof.

19 Claims, No Drawings

PHARMACEUTICAL COMPOSITIONS AND METHODS USING CERTAIN 4H-PYRANO (3,2-G) QUINOLINE COMPOUNDS

This invention relates to pharmaceutical compositions, methods for their preparation and methods of treatment using them.

UK Patent No. 2022078 discloses a number of pyranoquinolines which are indicated for use in the treatment of, inter alia, reversible airways obstruction. These compounds are described as being administered oesophageally or by inhalation. UK Patent application No. 2157291 discloses a pressurised aerosol formulation of one of these pyranoquinolines, known as nedocromil sodium, which is the disodium salt of 9-ethyl-6,9-dihydro-4,6-dioxo-10-propyl-4H-pyrano(3,2-g)quinoline-2,8-dicarboxylic acid, also for the treatment of reversible airways obstruction.

In general, the pyranoquinoline compounds disclosed in the above references are highly polar, hydrophilic molecules. As such they would not be expected to be absorbed through the skin to a sufficient extent to provide therapeutic levels of the compounds in the sub-epithelial tissues.

Surprisingly, however, we have now found that compositions containing as active ingredient, 9-ethyl-6,9-dihydro-4,6-dioxo-10-propyl-4H-pyrano(3,2-g)quinoline-2,8-dicarboxylic acid or a pharmaceutically acceptable derivative thereof are effective in the treatment of certain dermatological disorders when applied topically to the skin.

According to the invention there is provided a pharmaceutical composition comprising, as active ingredient, 9-ethyl-6,9-dihydro-4,6-dioxo-10-propyl-4H-pyrano(3,2-g)quinoline-2,8-dicarboxylic acid or a pharmaceutically acceptable derivative thereof in admixture with a pharmaceutically acceptable adjuvant or excipient, the composition being suitable for topical administration to a patient's skin but not suitable for administration orally or to the patient's eye.

Pharmaceutically acceptable derivatives of the active ingredient include pharmaceutically acceptable metal ion salts, such as alkali metal salts, eg the di-sodium and di-potassium salts, and alkaline earth metal salts, eg the calcium and magnesium salts. We especially prefer the di-sodium salt, which is commonly known as nedocromil sodium.

The composition may contain from 0.5 to 20% w/w, preferably from 1.0 to 10% w/w, eg 4% w/w, of the active ingredient.

We prefer the composition to be a cream. The cream may be a water-in-oil cream or, more preferably, an oil-in-water cream.

The cream preferably includes one or more emulsifying agents. Suitable emulsifying agents for oil-in-water creams include sodium, potassium, ammonium and triethanolamine soaps; polysorbates; and cationic, anionic and non-ionic emulsifying waxes. For water-in-oil creams, suitable emulsifying agents include calcium soaps, wool fat, wool alcohols, beeswax and certain sorbitan esters.

The cream generally contains an effective proportion of a pharmaceutically acceptable preservative or sterilising agent suitable for a cream. Examples of preservatives which may be used are chlorbutol, chlorocresol, methyl p-hydroxybenzoate (either alone or in combination with propyl p-hydroxybenzoate) and thiomersal.

The preservative may be present at a level of from about 0.05 to 1.0% w/w, more preferably from about 0.1 to 0.5%, eg 0.2%.

The cream may be buffered at a pH of from 3.0 to 7.0, preferably at a pH of from 4.0 to 6.5, and more preferably at a pH of from 5.0 to 6.0.

Thus, according to a preferred aspect of the invention, there is provided an oil-in-water pharmaceutical cream buffered at a pH of from 3.0 to 7.0 and comprising, as active ingredient, sodium 9-ethyl-6,9-dihydro-4,6-dioxo-10-propyl-4H-pyrano (3,2-g)quinoline-2,8-dicarboxylate.

The oil phase of the oil-in-water cream preferably comprises liquid paraffin. The oil phase preferably includes one or more emulsifying agents, e.g. a long chain alcohol, such as cetostearyl alcohol, or a fatty acid ester, such as self-emulsifying glyceryl monostearate. The oil phase may also include one or more emollients, eg isopropyl myristate and one or more additional surfactants, e.g. one or more cetomacrogol ethers. The oil phase preferably constitutes from 20 to 40% w/w of the cream.

The water phase may include a buffering agent, e.g. the salt of a weak acid. Suitable acids include carboxylic acids, e.g. acetic acid and particularly citric acid. Suitable salts include alkali metal salts, e.g. sodium or potassium.

The water phase may also include one or more bacteriocidal and/or fungicidal preservatives, eg potassium sorbate and methyl hydroxybenzoate.

The composition according to the invention may also be formulated as an ointment, a lotion or liniment, or as a dusting powder.

In ointments, the active ingredient is preferably finely-divided and dispersed in a waxy, fatty, protein or paraffin base, preferably a soft paraffin base. Liquid paraffin, hard paraffin, and wool fat may be included in the ointment base.

We prefer to use ointments containing a major proportion (e.g. 70–90% w/w) of a white or yellow soft paraffin and optionally minor proportions of a liquid paraffin (5–15% w/w) and of a hard paraffin (0–12% w/w).

The ointment may also contain other liquid components, e.g. water or polyethylene glycol to improve the consistency of the base, provide a solvent for the active ingredient so that the active ingredient may be sterilised by filtration and/or to alter the rate of release of the active ingredient from the base.

Lotions and liniments preferably comprise a solution or dispersion of the active ingredient in an aqueous or oily base. A suitable preservative may be included in the formulation. Where pastes, gels or emulsions are desired, a thickening agent may be incorporated in an aqueous base. Suitable thickening agents include cross-linked polymers, soluble cellulose derivatives and polyvinyl alcohol.

Dusting powders may contain two or more ingredients intimately mixed in fine powder form. Alternatively, the active ingredient may be applied as a solution or suspension in a liquid carrier to the surface of a solid carrier and the coated particles dried. Examples of solid carriers, which are normally sterilised, are talc, starch, lactose, zinc oxide, light kaolin and calcium carbonate.

Where solid particles of the active ingredient are present, e.g. in a suspension or dispersion or in a powder formulation, it is preferred that these have a mean particle size in the range 0.01 to 10 micrometers.

The compositions according to the invention may be prepared by mixing the ingredients, e.g. by dry mixing or by grinding the solid ingredients together, or by emulsifying an aqueous solution of the active ingredient with an appropriate oil base. The final pH of the solution may be controlled by the addition of an appropriate quantity of acid or base.

Creams may be made by dissolving the active ingredient in water buffered at the desired pH and adding the solution to the molten oil phase ingredients in a homogeniser at a temperature of from about 40° to 90° C. After homogenisation and cooling, the cream may be filled into suitable receptacles, e.g. tubes.

The composition is preferably administered to the skin of a patient merely by smearing or spreading the cream over the skin which is affected or likely to be affected.

The frequency of application of the composition will depend upon the severity of the disorder to be treated and the area of the skin over which it extends. Repeated applications may be made at intervals during the day, eg from 1 to 6 times, preferably twice, a day. The composition may be applied prophylactically, but is more usually applied to an area which is already affected.

The composition finds use in the treatment of various dermatological disorders in mammals, notably man, cats, dogs and horses, including conditions which involve skin mast cells and/or delayed (cellular) hypersensitivity reactions and/or which involve inflammation.

The composition is of particular use in the treatment of atopic eczema in man.

Other specific conditions in man and other animals which may be treated include contact sensitivity, e.g. to chromium, nickel or an antibiotic; drug eruptions; psoriasis; dermatitis; apthous ulcers; Behcet's syndrome; pemphigus; urticaria; urticaria pigmentosa; the ulcers of Crohn's disease; pyoderma gangrenosum; chronic skin ulcers; burns; bee and wasp stings; herpetic infections; and dermatological disorders, e.g. systemic sclerosis (also known as systemic scleroderma), morphoea (also known as circumscribed or localised scleroderma) and dermal nodular fibrosis (also known as dermatofibroma), which involve excessive fibrosis.

Thus, according to a further aspect of the invention, there is provided a method of treatment of a dermatological disorder selected from the group consisting of atopic eczema, contact sensitivity, drug eruptions, psoriasis, dermatitis, apthous ulcers, Behcet's syndrome, pemphigus, urticaria, urticaria pigmentosa, the ulcers of Crohn's disease, pyoderma gangrenosum, chronic skin ulcers, burns, bee and wasp stings, herpetic infections, and dermatological disorders which involve excessive fibrosis, which comprises topical administration to the skin of a patient suffering from such a disorder of a therapeutically effective quantity of 9-ethyl-6,9-dihydro-4,6-dioxo-10-propyl-4H-pyrano(3,2-g)quinoline-2,8-dicarboxylic acid or a pharmaceutically acceptable derivative thereof.

The amount of the active agent to be administered will of curse vary with the condition to be treated, the animal or patient to be treated, the particular derivative used and the mode of administration. However, generally satisfactory results can be achieved when the active agent is administered at a dosage of from about 1 to 100, and preferably 10 to 75mg per kg of animal body weight. For man the indicated daily dosage is in the range of from 1mg to 3500mg, preferably 1mg to 1500mg and more preferably from 1 mg to 600 mg, which may be administered in divided doses from 1 to 6 times a day. As is usual when treating a skin condition topically, e.g. using an cream, the dosage is difficult to control, but will depend in general on the size and condition of the area to be treated.

The invention is illustrated, but in no way limited, by the following Examples.

Example 1: Oil-in-Water Cream

| Ingredients | % w/w |
|---|---|
| Oil phase | |
| Glyceryl Monostearate BP | 4.0 |
| Cetostearyl Alcohol BP | 4.0 |
| Liquid Paraffin BP | 10.0 |
| Isopropyl Myristate BP | 5.0 |
| Cremophor A6* | 2.0 |
| Cremophor A25* | 2.0 |
| Propyl Hydroxybenzoate BP | 0.1 |
| Aqueous phase | |
| Methyl Hydroxybenzoate BP | 0.1 |
| Potassium Sorbate BP | 0.2 |
| Puried Water BP (low metal) | 67.22 |
| Sodium Acid Citrate BP | 1.3 |
| Sodium Hydroxide BP | 0.08 |
| Active ingredient Sodium 9-ethyl-6,9-dihydro-4,6-dioxo-10-propyl-4H—pyrano(3,2-g)quinoline-2,8-dicarboxylate | 4.0 |

*Cremophor A6 and Cremophor A25 are Trade Marks.

Method

The oil phase components are placed in a mixing bowl and melted with stirring at 60°-70° C.

The active ingredient is added to the buffered aqueous phase, dissolved under gentle heating and then the warm aqueous layer added to the oil phase with vigorous stirring. When the addition and homogenisation is complete, the mixture is allowed to cool under gentle agitation and then filled into 20 ml tues at ambient temperature.

Example 2: Oil-in-Water Cream

| Ingredients | % w/w |
|---|---|
| Oil phase | |
| Glyceryl Monostearate BP | 4.0 |
| Cetostearyl Alcohol BP | 4.0 |
| Liquid Paraffin BP | 15.0 |
| Cremophor A6* | 2.0 |
| Cremophor A25* | 2.0 |
| Propyl Hydroxybenzoate BP | 0.1 |
| Aqueous phase | |
| Methyl Hydroxybenzoate BP | 0.1 |
| Potassium Sorbate BP | 0.2 |
| Puried Water BP (low metal) | 67.22 |
| Sodium Acid Citrate BP | 1.3 |
| Sodium Hydroxide BP | 0.08 |
| Active ingredient Sodium 9-ethyl-6,9-dihydro-4,6-dioxo-10-propyl-4H—pyrano(3,2-g)quinoline-2,8-dicarboxylate | 4.0 |

*Cremophor A6 and Cremophor A25 are Trade Marks.

Method

This composition was prepared by the method of Example I and showed improved preservation characteristics.

Example 3: Ointment

| Ingredients | % w/w |
| --- | --- |
| Liquid Paraffin BP | 10 |
| Wool Fat BP | 10 |
| White Soft Paraffin BP | 70 |
| Active Ingredient<br>Sodium 9-ethyl-6,9-dihydro-4,6-dioxo-10-propyl<br>-4H—pyrano(3,2-g)quinoline-2,8-dicarboxylate | 10 |

Method

Prepared by dispersing finely divided active ingredient in a molten mixture of the other component in a mixing bowl at 60°–70° C. After homogenisation, the mixture is allowed to cool and then filled into 20ml tubes at ambient temperature.

Example 4: Oily Lotion

| Ingredients | % w/w |
| --- | --- |
| Arachis oil | 85 |
| Active Ingredient<br>Sodium 9-ethyl-6,9-dihydro-4,6-dioxo-10-propyl<br>-4H—pyrano(3,2-g)quinoline-2,8-dicarboxylate | 15 |

Method

Prepared by dispersing the finely divided active ingredient in the oil.

Example 5: Dusting Powder

| Ingredients | % w/w |
| --- | --- |
| Zinc oxide | 25 |
| Purified Talc | 10 |
| Sterilisable Maize Starch | 55 |
| Active Ingredient<br>Sodium 9-ethyl-6,9-dihydro-4,6-dioxo-10-propyl<br>-4H—pyrano(3,2-g)quinoline-2,8-dicarboxylate | 10 |

Method

Prepared by grinding together the various ingredients.

Example 6: Skin Permeation Measurements Penetration of active ingredient through hairless mouse and human skin has been demonstrated in the following tests for various formulations: Hairless mice, of either sex, aged 8–12 weeks were sacrificed by cervical dislocation, the dorsal skin excised and subcutaneous fat removed with minimal handling. Human epidermal membranes were prepared by immersing whole (epidermis plus dermis) skin in water at 60° C. for 30 seconds, removing and gently teasing off the epidermis by means of blunt forceps. Care was taken to ensure minimal handling of the thin membrane. Samples were then mounted, epidermal side uppermost, onto a glass horizontal diffusion cell, a donor chamber fixed in position and clamped. The receiving medium was 50% aqueous ethanol (v/v) and the cells were mounted in a thermostatically controlled water bath at 37° C.

The formulation under test was applied evenly to the epidermal side of the sample. After a predetermined time, the receiving medium was removed, filtered and analysed for the active ingredient by high pressure liquid chromatography (HPLC).

We claim:

1. A pharmaceutical composition in the form of a cream, ointment, liniment, or lotion for treatment of a dermatological disorder, said composition comprising, as active ingredient, an effective proportion of 9-ethyl-6,9-dihydro-4,6-dioxo-10-propyl-4H-pyrano(3,2 g)quinoline-2,8-dicarboxylic acid or a pharmaceutically acceptable derivative thereof in admixture with a pharmaceutically acceptable adjuvant or excipient, adapted for topical administration to a patient's skin.

2. A composition according to claim 1, wherein the active ingredient is in the form of a pharmaceutically acceptable metal ion salt.

3. A composition according to claim 1, wherein the active ingredient is nedocromil sodium.

4. A composition according to claim 1, which contains from 0.5 to 20% w/w of active ingredient.

5. A composition according to claim 1, which contains from 1.0 to 10% w/w of active ingredient.

6. A composition according to claim 1, which is a cream.

7. A composition according to claim 6, which is an oil-in-water cream.

8. A composition according to claim 6, which has a pH of between 3.0 and 7.0.

9. A composition according to claim 6, wherein the pH is between 4.0 and 6.5.

10. A composition according to claim 6, wherein the pH is between 5.0 and 6.0.

11. An oil-in-water pharmaceutical cream buffered at a pH of from 3.0 to 7.0 and comprising, as active ingredient, sodium 9-ethyl-6,9-dihydro-4,6-dioxo-10-propyl-4H-pyrano (3,2-g)quinoline-2,8-dicarboxylate.

12. A composition according to claim 1, which is in the form of an ointment.

13. A composition according to any one of claim 1, which is in the form of a liniment or lotion.

14. A method of treatment of a dermatological disorder selected from the group consisting of atopic eczema, contact sensitivity, drug eruptions, psoriasis, dermatitis, apthous ulcers, Behcet's syndrome, pemphigus, urticaria, urticaria pigmentosa, the ulcers of Crohn's disease, pyoderma gangrenosum, chronic skin ulcers, burns, bee and wasp stings, herpetic infections, and dermatological disorders which involve excessive fibrosis, which comprises topical administration to the skin of a patient suffering from such a disorder of a therapeutically effective quantity of 9-ethyl-6,9-dihydro-4,6-dioxo-l0-propyl-4H-pyrano(3,2-g)quinoline-2,8-dicarboxylic acid or a pharmaceutically acceptable derivative thereof.

15. A method according to claim 14, wherein the disorder to be treated is atopic eczema.

16. A method according to claim 14, wherein the disorder to be treated is selected from the group comprising contact sensitivity, drug eruptions, psoriasis, dermatitis, apthous ulcers, Behcet's syndrome, pemphigus, urticaria, urticaria pigmentosa, the ulcers of Crohn's disease, pyodermagangrenosum and chronic skin ulcers.

17. A method according to claim 14, wherein the disorder to be treated is selected from the group comprising burns, bee and wasp stings, and herpetic infections.

18. A method according to claim 14, wherein the disorder to be treated is a dermatological disorder which involves excessive fibrosis.

19. A method according to claim 18, wherein the disorder to be treated is selected from the group consisting of systemic scleroderma, morphoea and dermal nodular fibrosis.

* * * * *